United States Patent [19]

Crawford et al.

[11] Patent Number: 4,898,465
[45] Date of Patent: Feb. 6, 1990

[54] GAS ANALYZER APPARATUS

[75] Inventors: A. Gerrit Crawford, White Bear Lake; Douglas C. Morrison, Shoreview, both of Minn.

[73] Assignee: Medical Graphics Corporation, St. Paul, Minn.

[21] Appl. No.: 302,919

[22] Filed: Jan. 30, 1989

[51] Int. Cl.$^4$ .............................................. G01N 21/66
[52] U.S. Cl. .................................... 356/311; 313/619; 356/313
[58] Field of Search ................ 356/311, 313; 313/424, 313/619, 634 (U.S. only)

[56] References Cited

U.S. PATENT DOCUMENTS 4,801,209  1/1989  Wadlow .......................... 356/311 X Primary Examiner—Vincent P. McGraw
Attorney, Agent, or Firm—Haugen and Nikolai

[57] ABSTRACT

A cold-cathode gas discharge device is coupled between a gas sample inlet and a high vacuum and includes spaced-apart electrodes which, when coupled across a high voltage DC power supply, causes a glow-discharge to be set up within the device with the intensity of the emitted light being proportional to the percentage of a given gas contained within a gas mixture introduced through the sampling inlet. In accordance with the present invention, the glow-discharge device contains a tubular pathway which is bent at a point intermediate the spaced electrodes so that they are not co-linear along the tubular path. A photodetector is sighted coaxially with the downstream leg of the bent pathway and, as such, senses the light emitted in a longitudinal direction rather than in a transverse direction. As such, errors due to fogging of the pathway over time by electrode material or the like and movement of the cathode dark-spaced and Faraday dark-space within the tube do not alter the measurable radiation.

7 Claims, 1 Drawing Sheet

GAS ANALYZER APPARATUS

BACKGROUND OF THE INVENTION

I. Field of the Invention

This invention relates generally to a gas analyzer apparatus, and more particularly to a gas analyzer of the cold-cathode glow-discharge type in which a gas sample introduced into an ionization chamber produces a glow whose intensity varies with a given gas concentration and whose spectrum varies with a given gas mixture.

II. Discussion of the Prior Art

In prior art gas analyzers of the so-called "Geisler tube" type, an unknown gas mixture is introduced into one end of a straight tube while a high vacuum is maintained within the tube by a suitable vacuum pump. When an appropriate high voltage is applied between the cathode and anode electrodes, ionization of the gas occurs, resulting in a glow and the emission of radiant energy in the infrared, visible and ultraviolet spectrum. By positioning a photodetector circuit adjacent the side wall of the spectrum-transparent tube, a signal is produced which, ideally, is proportional to the concentration of certain gases within the unknown mixture. Such prior art gas analyzers also utilize an optical filter disposed between the glow tube and the photodetector which is intended to pass a band of wavelengths unique to a particular gas. Thus, for example, if the device is to be used to measure the amount of nitrogen present in an air sample, it has been common practice to utilize a UV filter between the glow tube and the photodetector in that pure nitrogen classically exhibits a peak in the spectrum corresponding to UV wavelengths. This practice neglects the facts that: (1) a mixture of nitrogen and oxygen or carbon dioxide results in a shift in the peak radiation intensity toward the red wavelengths, and (2) that photodetectors exhibit poor sensitivity to ultraviolet and blue wavelengths.

The above-described prior art gas analyzer suffers from four major problems bearing upon its ability to provide consistent results over time. First of all, the walls of the tube tend to become clouded by impurities often introduced along with the sample being investigated or from the erosion of the electrodes caused by ion bombardment. This clouding results in a substantial decrease in sensitivity and premature replacement.

The second major defect centers around the fact that in a cold-cathode glow-discharge tube there is a variegated light pattern (banding). In particular, near the anode electrode a region called the "positive-column" develops. It is often also referred to as the plasma and consists of a series of rings separated by dark areas. Next to it is a region of low light intensity referred to as the "Faraday dark-space". As one moves toward the cathode, adjacent to the Faraday dark-space is the so-called "negative-glow" region, followed next by the cathode dark-space (Crookes dark-space) and finally the cathode glow region. It has been found that these ring-like regions do not remain stable but are subject to some movement or jitter within the tube, especially with the routinely encountered oscillatory changes in vacuum levels. Such jitter is a source of noise which necessarily detracts from the accuracy of the readings achievable using the device when the photodetector is oriented transverse to the direction of gas flow through the side wall of the glow-discharge tube.

The third limitation relates to the observation that nitrogen, in combination with oxygen, exhibits pronounced emissions in the orange and red spectra rather than in the ultraviolet. Conversely, major ultraviolet emissions appear most abundant with oxygen rather than nitrogen (the gas of interest).

Fourthly, commercial ultraviolet filters not only absorb most visible light, but also as much as 80% of the ultraviolet. When coupled with the typical insensitivity to ultraviolet of photodetectors, a very small portion of the actual emission is detected. This results in extremely poor signal-to-noise ratios.

OBJECTS

It is thus an object of the present invention to provide an improved gas analyzer of the cold-cathode glow-discharge type.

Another object of the invention is to provide a gas analyzer of the cold-cathode glow-discharge type in which the readings do not drift over time with clouding of the wall surface of the glow-discharge tube.

A still further object of the invention is to provide a gas analyzer of the cold-cathode glow-discharge type in which shifts in the light pattern emanating from the glow tube do not adversely impact the accuracy of the readings obtained from the analyzer.

An additional object of the invention is to provide a gas analyzer of the cold-cathode glow-discharge type in which a photodetector is disposed within, and signed coaxially through, the appropriate portion of the plasma stream.

A further additional object of the invention is to provide a gas analyzer of the cold-cathode glow-discharge type in which a high intensity and highly detectable emission is produced by nitrogen, when in the presence of oxygen.

A still further additional object of the invention is to provide a gas analyzer of the cold-cathode glow-discharge type in which a spectral filter is not necessary to discriminate nitrogen in the presence of oxygen.

A final additional object of the invention is to provide a gas analyzer of the cold-cathode glow-discharge type in which vacuum level fluctuations (both long term and pulsatile) are self-compensating.

SUMMARY OF THE INVENTION

In accordance with the present invention there is provided a cold-cathode, glow-discharge device having a body within which is located a tubular passage, a hollow cathode electrode at one end of the passage, and a hollow anode electrode at the other end. Means are provided for introducing a gas mixture through the cathode end of the device. A predetermined negative pressure is maintained within the tubular passage by virtue of a vacuum pump or other source of negative pressure coupled to the anode end of the device. Rather than utilizing a straight tube, in the present invention the passage within the body is bent at an angle of about 30° or greater with the photodetector being positioned in a generally coaxial alignment with the anode end of the device so as to effectively sight the length of one straight leg segment of the tubular passage. Because of the presence of the bend, contaminants entering the system with the test sample and accelerated towards the anode by electromotive attraction, do not negotiate the bend, but instead, travel in a straight line path and impinge upon the wall of the path at the bend. Because the photodetector is aligned co-axially with a straight segment of the tubular path proximate to the anode end thereof rather than being disposed transverse to the direction of gas flow through the passage, the light energy which it receives is the totality of the glow within the path segment aligned with the photodetector and it does not matter that the glow rings may be jittering within the tube.

Another feature of the present invention is that higher excitation currents can be employed than in prior art Geisler tube gas analyzers, resulting in increased intensity of optimally detectable radiation. In prior art systems, this would not be possible due to unacceptable increases in banding and the poor thermal characteristics of spectrally transparent materials.

As previously discussed, the prior art teaches a spatial separation of glow-discharge regions into negative-glow (proportional to oxygen and carbon dioxide concentrations) and positive-glow (proportional to nitrogen) bands. The curve or bend in the tubular path embodied in the present invention, optically isolates the negative-glow from the positive-glow and the photodetector. This obviates the need for spectral filters and the concomitant decreases in the analyzer's signal-to-noise ratio.

It is also a feature of the present invention that the electrical current flowing through the glow tube is sensed and converted to a control voltage, with that control voltage being applied to the amplifier circuit of the photodetector as an automatic gain control signal. As such, moderate changes in light intensity occasioned by variations in the pressure, such as those generally caused by the pumping action of the vacuum pump are compensated for in the detector circuitry and do not detract from the accuracy of the output readings of the analyzer.

The foregoing objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
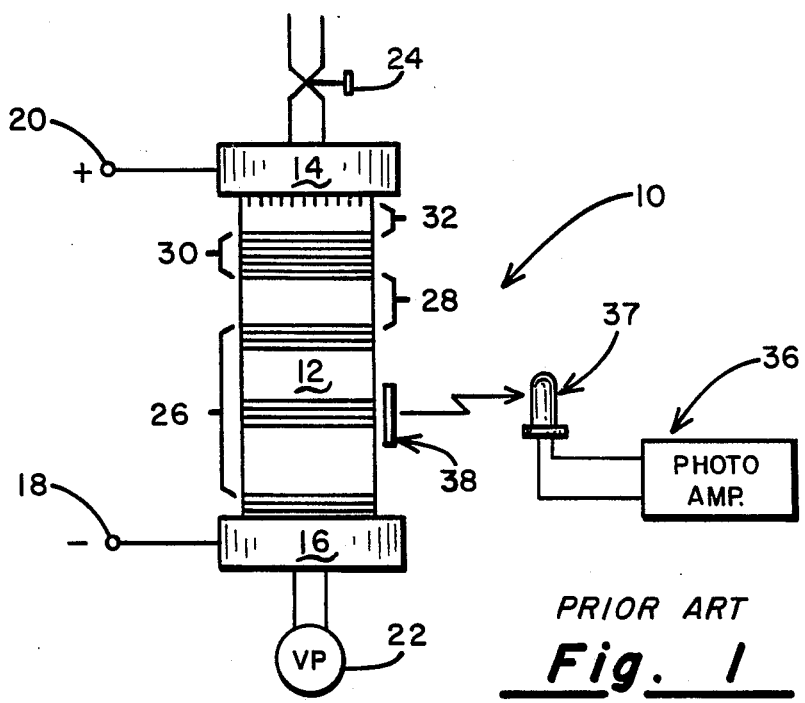
FIG. 1 illustrates by means of a schematic a typical prior art cold-cathode glow tube gas analyzer.

Referring to FIG. 1, there is illustrated a typical prior art Geisler tube type gas analyzer and it is indicated generally by numeral 10. It is seen to comprise a quartz glass tube 12 extending between an anode electrode 14 and a cathode electrode 16. These electrodes are adapted to be connected at terminals 18 and 20 to a high voltage DC source (not shown). A suitable means, here shown as a vacuum pump 22 is coupled to the interior of the tube 12 so as to maintain a predetermined low pressure within the tube. A gas sample, such as air, may be introduced through a needle valve 24 into the interior of the tube 12. By appropriate setting of the needle valve 24, a desired flow rate can be maintained while the vacuum pump 22 continues to establish the requisite negative pressure within the tube.

When the appropriate voltage and current is applied and a gas is present within the partially evacuated tube 12, a well-documented glow condition is established within the tube. Specifically, immediately above the anode electrode 14 is the positive-column or plasma region 26. Next to it is the "Faraday dark-space" 28. As one moves closer to the cathode, the so-called "negative-glow" region 30 is encountered followed by the cathode dark-space 32 and finally the cathode glow region 34.

In a conventional prior art gas analyzer of the type described, a phototube/photodetector circuit 36 is positioned adjacent the side wall of the tube 12, usually in the positive-column region 26 for sensing the light energy being emitted through the side wall. Where one is using the analyzer to identify a particular concentration of a constituent gas in the mixture, an optical filter, as at 38, is generally interposed between the glow tube 12 and the photodetector 37. For example, where the gas analyzer is intended to monitor the nitrogen concentration in air, it has been a common practice to use a UV filter as the optical filter 38. This may be due to a misconception based on the fact that nitrogen gas by itself when examined by a spectrum analyzer exhibits a marked peak in the UV band. When mixed with $O_2$ or $CO_2$, however, the plasma is partially quenched causing the emitted radiation in the positive column to shift the peak intensity to the red portion of the spectrum.

As was mentioned in the introductory portion of this patent specification, the prior art device described in FIG. 1 suffers from several major drawbacks. First of all, any impurities in the air sample introduced through the needle valve 24 tend to coat the side wall of the tube 12, clouding the quartz tube and affecting the light transmission through it. In addition, because the photodetector 37 is positioned adjacent the side wall of the tube, any movement of the glow rings in the positive-column region have the effect of introducing noise into the photodetector circuit. This movement is not due to changes in gas concentration, but instead, to pressure variations within the tube 12 which may, for example, result from the pulsatile action of the vacuum pump 22.

Figure 2:
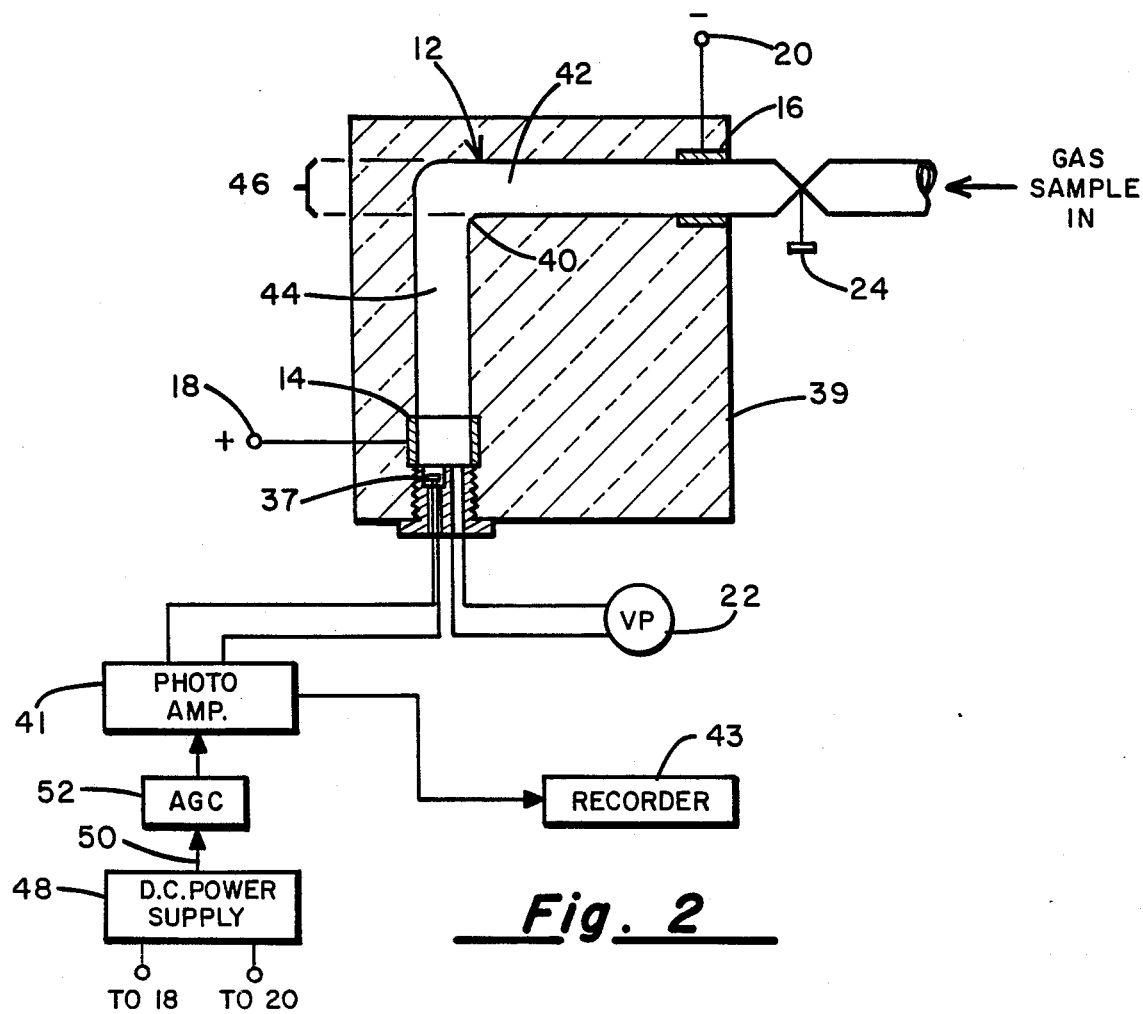
FIG. 2 illustrates a preferred embodiment of the present invention.

The above discussion of the prior art gas analyzer device assists in understanding the advantages and improvements afforded by the present invention, which is represented by the mechanical and electrical schematic drawing of FIG. 2. The principal difference between the prior art and the present invention resides in the fact that the cold-cathode gas discharge path through the housing block 39 is bent at a predetermined angle at a location between the cathode electrode 16 and the anode electrode 14. In FIG. 2, the path 12 is shown as being bent at a 90° angle at 40, but it is to be understood that any angle greater than about 30° can be used. The bend effectively divides the glow path into a first leg 42 and a second leg 44. A photodetector 37 is aligned coaxially with the leg 44 and, as such, "views" the entirety of the glow within the leg or segment 44. Hence, any jitter or movement of the glow rings or exaggeration of the bands, within the path do not vary the light energy impinging on the photodetector 37. The photodetector element 37 is coupled to a conventional amplifier circuit 41 driving a utilization device, e.g., a recorder 43.

Because of the presence of the bend 40, any contamination present in the gas sample passing through the needle valve 24 and accelerated by the high voltage present between the cathode electrode 16 and the anode electrode 14 cannot negotiate the bend and will impinge on the wall of the housing block identified by bracket 46. Thus, the deposition of the contaminants at that location does not effect a change in the sensitivity of radiation impinging on photodetector 37.

The inclusion of the bend 40 also obviates the need to include an optical filter like filter 38 in FIG. 1 between the glow path and the photodetector 37. The bend, itself, functions as an optical "filter" by displacing the negative-column from the detector's line-of-sight.

The coaxial relationship of the photodetector 37 to the glow path segment 44 also renders moot the problem of increased banding with increases in excitation current. However, to accommodate increased current (which results in a desirable increase in spectral radiation), special considerations must be given to the materials from which the analyzer is fabricated. The electrodes require a material with extremely high electrical and thermal conductivity and high temperature resistance, such as graphite or tungsten. The body 39 should be fabricated from a material exhibiting extremely low electrical conductivity and coefficient of thermal expansion but with high thermal conductivity and machinability. Boron nitride has been found to be exceptionally suitable for the specified application. The photodetector employed is preferably a semiconductor photodetector having a spectral response peaking in the red portion of the spectrum, however, limitation thereto is not required.

Another feature of the present invention involves the monitoring of the current drawn from the DC power supply 48 by the glow tube 12 and developing a control signal on line 50 proportional thereto which, through an automatic gain control circuit 52, is used to adjust the gain of the amplifier 41 associated with the photodetector 37. This is a valuable feature when it is considered that the light output from the gas discharge tube 12 is affected by both the vacuum level and the gas species being analyzed. By sampling the current drawn through the discharge tube, which is proportional to the vacuum level within the tube, and by using the resulting control signal to modify the gain of the photodetector amplifier, shifts in vacuum level are effectively eliminated as a possible cause of misinterpretation of a gas analyzer reading as being due to a change in concentration.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. In a gas analyzer of the type incorporating a tubular glow-discharge path having a cathode electrode at a first end of said path and an anode electrode at the other end, with means for introducing an unknown gas mixture into the interior of said tubular path while maintaining a predetermined negative pressure therein, and photodetector means positioned to intercept light emanating from said tubular path for producing a signal indicative of the concentration of a particular gas constituent of said mixture, the improvement comprising: a bend formed in said tubular path such that said anode electrode and said cathode electrode are non-colinear, said photodetector means being disposed in coaxial alignment with said tubular path proximate said anode electrode.

2. The gas analyzer as in claim 1 wherein said tubular path is bent to form two leg segments joined to one another at an angle greater than about 30°.

3. Apparatus for measuring the concentration of a particular gas constituent in a gaseous mixture, comprising:
   (a) a cold-cathode glow discharge device having a positive electrode and a negative electrode respectively located at opposite ends of a glow discharge path, said path comprising first and second segments joined at a predetermined angle intermediate said opposed ends;
   (b) means for maintaining a negative pressure within said glow discharge path of said device;
   (c) means for introducing a sample of said gaseous mixture into said glow discharge path;
   (d) means for applying a predetermined voltage between said positive and negative electrodes sufficient to cause said gaseous mixture to glow and emit light; and
   (e) a photosensitive device aligned coaxially with one of said first and second segments of said glow discharge path for receiving the light emitted from an end of said one segment.

4. The gas analyzer as in claim 3 wherein said glow discharge path is formed in a block of boron nitride.

5. The gas analyzer as in claim 4 wherein said first and second electrodes are formed from tungsten.

6. The gas analyzer as in claim 3 wherein said photosensitive device comprises a semiconductor photodetector having primary sensitivity to radiation in the red portion of the spectrum.

7. The gas analyzer as in claim 3 wherein said means for applying a predetermined voltage between said first and second electrodes comprises:
   (a) a direct current power supply having first and second output terminals respectively connected to said first and second electrodes;
   (b) means for sensing the current being drawn through said glow discharge path and producing a control signal proportional thereto; and
   (c) means for applying said control signal to said photodetector means for adjusting the gain of said photodetector means to compensate for pressure changes in said glow discharge path.

* * * * *